(12) United States Patent
West

(10) Patent No.: US 10,207,054 B2
(45) Date of Patent: Feb. 19, 2019

(54) MIXING PEN NEEDLE

(71) Applicant: Becton, Dickinson and Company, Franklin Lakes, NJ (US)

(72) Inventor: Robert E. West, Basking Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 154 days.

(21) Appl. No.: 15/268,252

(22) Filed: Sep. 16, 2016

(65) Prior Publication Data

US 2017/0000947 A1    Jan. 5, 2017

Related U.S. Application Data

(62) Division of application No. 13/869,545, filed on Apr. 24, 2013, now Pat. No. 9,468,725.

(51) Int. Cl.
| | | |
|---|---|---|
| *A61M 5/24* | (2006.01) | |
| *A61M 5/32* | (2006.01) | |
| *A61M 5/28* | (2006.01) | |
| *A61M 5/14* | (2006.01) | |
| *A61M 5/315* | (2006.01) | |
| *A61M 5/20* | (2006.01) | |
| *A61M 5/19* | (2006.01) | |

(Continued)

(52) U.S. Cl.
CPC .......... *A61M 5/2448* (2013.01); *A61J 1/201* (2015.05); *A61J 1/2027* (2015.05); *A61J 1/2096* (2013.01); *A61M 5/1407* (2013.01); *A61M 5/19* (2013.01); *A61M 5/2066* (2013.01); *A61M 5/284* (2013.01); *A61M 5/31596* (2013.01); *A61M 5/3294* (2013.01); *A61J 1/20* (2013.01); *A61J 1/2089* (2013.01); *A61M 5/204* (2013.01); *A61M 5/31551* (2013.01); *A61M 5/3213* (2013.01); *A61M 5/347* (2013.01); *A61M 2005/2451* (2013.01); *A61M 2005/2474* (2013.01); *A61M 2005/3128* (2013.01); *A61M 2205/581* (2013.01); *A61M 2205/582* (2013.01)

(58) Field of Classification Search
CPC ...... A61M 5/284; A61M 5/3294; A61M 5/19; A61M 5/2448; A61M 5/1407; A61M 5/31596; A61M 5/2066; A61M 2005/2474; A61M 2005/2451; A61M 2005/1787; A61M 2005/2013; A61J 1/20; A61J 1/2089
See application file for complete search history.

(56) References Cited

U.S. PATENT DOCUMENTS 3,604,410 A    9/1971    Whitacre
4,014,330 A  *  3/1977    Genese ............... A61M 5/2429
                                                    604/88

(Continued)

FOREIGN PATENT DOCUMENTS

JP           2012528640 A    11/2015
WO          WO-9325251 A1    12/1993
WO          WO-2012160166    11/2012

*Primary Examiner* — Nathan R Price
*Assistant Examiner* — Anh Bui
(74) *Attorney, Agent, or Firm* — Dickinson Wright PLLC

(57) ABSTRACT

An injection device is provided with dual medicament chambers and a mixing pen needle assembly, whereby predetermined dosages of two medicaments can be provided to a mixing reservoir in the pen needle assembly and delivered simultaneously with the injection device.

13 Claims, 4 Drawing Sheets

(51) Int. Cl.
    *A61J 1/20*     (2006.01)
    *A61M 5/34*     (2006.01)
    *A61M 5/31*     (2006.01)

(56) References Cited

U.S. PATENT DOCUMENTS

| | | |
|---|---|---|
| 5,314,412 A | 5/1994 | Rex |
| 5,354,284 A * | 10/1994 | Haber .................... A61M 5/19 |
| | | 604/191 |
| 5,378,233 A | 1/1995 | Haber et al. |
| 5,445,614 A | 8/1995 | Haber et al. |
| 5,478,323 A * | 12/1995 | Westwood .............. A61M 5/19 |
| | | 604/191 |
| 5,542,760 A | 8/1996 | Chanoch et al. |
| 5,961,495 A | 10/1999 | Walters et al. |
| 6,096,010 A | 8/2000 | Walters et al. |
| 6,221,053 B1 | 4/2001 | Walters et al. |
| 6,248,095 B1 | 6/2001 | Giambattista et al. |
| 6,277,099 B1 | 8/2001 | Strowe et al. |
| 6,585,698 B1 | 7/2003 | Packman et al. |
| 6,932,794 B2 | 8/2005 | Giambattista et al. |
| 6,936,032 B1 | 8/2005 | Bush, Jr. et al. |
| 7,018,364 B2 | 3/2006 | Giambattista et al. |
| 7,645,264 B2 | 1/2010 | Marsh et al. |
| 7,850,663 B2 | 12/2010 | Sullivan et al. |
| 2006/0229562 A1 | 10/2006 | Marsh et al. |
| 2009/0240232 A1* | 9/2009 | Gonnelli ........... A61M 5/14526 |
| | | 604/506 |
| 2010/0286605 A1 | 11/2010 | Klug et al. |
| 2011/0282324 A1 | 11/2011 | Kurokawa et al. |
| 2012/0172793 A1 | 7/2012 | Cronenberg et al. |

* cited by examiner

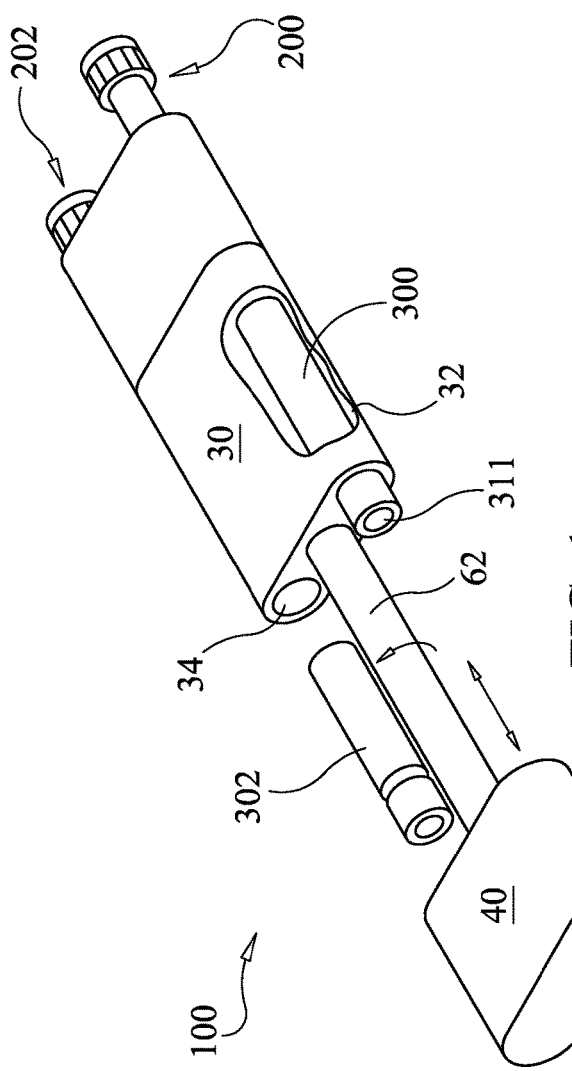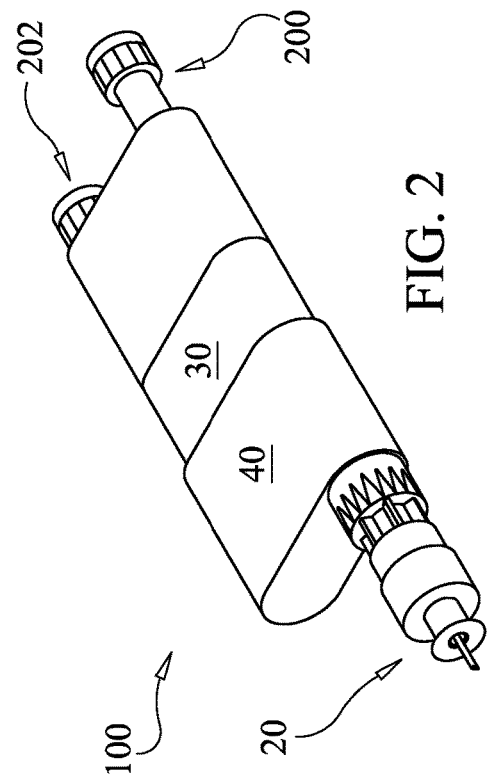

MIXING PEN NEEDLE

RELATED APPLICATION

This application is a divisional of U.S. patent application Ser. No. 13/869,545, filed on Apr. 24, 2013, which is hereby incorporated by reference in its entirety.

FIELD OF THE INVENTION

The invention is in the field of injection devices. Specifically, the disclosure pertains to a medication pen adapted to deliver a mixture of separately dosed medications with a single injection.

DESCRIPTION OF THE RELATED ART

Medication pens are widely used for self-administered injectable drugs such as insulin. And patients are often required to take medications in combination with each other. For example, insulin is co-administered with glucagon like peptide ("GLP"). Therefore, it would be desirable if medications could be mixed at the time of use and co-administered with the convenience of a medication pen. The conventional thinking in the art is that a compact medication delivery device capable of mixing and delivering two medications with a pen needle would require a complicated valved manifold to keep the two medications from mixing.

U.S. Pat. No. 5,542,760, to Chanoch et al, incorporated by reference in its entirety, describes a syringe filler for mixing different types of insulin in a syringe. A syringe is inserted into a syringe holder assembly which is rotatably mounted on a housing for containing two medication cartridges. Using the syringe holder, the syringe may be aligned with either of the two medication cartridges. A separate dose is loaded into the syringe from each cartridge, thus avoiding the complications associated with free-mixing different types of insulin for diabetic patients who require different types of insulin.

The disadvantage of the device is that the syringe must be separately handled to conduct the filling process and the injection. Therefore, it would be desirable to have a pen-type device that can deliver mixtures of individually dosed medications.

U.S. Pat. No. 7,645,264, to Marsh et al., also incorporated by reference, discloses a medication pen having a collapsible secondary reservoir in addition to a primary reservoir (such as a cartridge). The secondary reservoir is used to provide a mechanical advantage when delivering medication to tissue layers encountering relatively high backpressure such as an intradermal space. Medication flows from the cartridge of a pen device to the axially aligned secondary reservoir in the pen needle with little or no backpressure. An injection is administered by collapsing the collapsible secondary reservoir and the delivery force of the injection is controlled by the relative sizes of the primary and secondary reservoirs. However, the pen-type device disclosed does not house more than one cartridge nor is the secondary reservoir used to mix different medications.

The present invention improves over the aforementioned prior art by providing an injection device having a pen needle assembly that can be installed on a housing containing a plurality of medication compartments, such that medications individually dosed from the plurality of medication compartments can be mixed in the pen needle assembly and delivered simultaneously.

SUMMARY OF THE INVENTION

Thus, in one aspect, the invention is a medication pen comprising: a pen body having a distal end and a proximal end, and having a first medication compartment and a second medication compartment. First and second dosing mechanisms located proximally of the medication compartment are engaged with first and second dosage plungers engaged in the respective first and second medication compartments. A movable housing received on the distal end of the pen body is adapted to be received in first and second positions on the pen body and a pen needle assembly is received on the distal end of the movable housing. The pen needle assembly comprises a patient end needle, a filler needle, and a collapsible mixing reservoir intermediate and accessed by the patient end needle and the filler needle. The movable housing is movable between a first position in which the filler needle is in fluid communication with the first medication compartment and a second position in which the filler needle is in fluid communication with the second medication compartment.

The user attaches the pen needle assembly to the movable housing and uses the dosing mechanism to partially fill the mixing reservoir with medication from the first medication compartment. The movable housing is then moved to the second position and the filling step is repeated to fill the mixing reservoir with medication from the second medication compartment. Inserting the patient end needle into the patient's tissue and pressing distally toward the injection site collapses the mixing reservoir and forces medication in the mixing reservoir through the patient end needle during an injection.

Although described herein in connection with the co-administration of insulin and GLP, the device may be used with other medications and combinations suitable for use with a medication pen.

BRIEF DESCRIPTION OF THE DRAWINGS

FIG. 1 is an exploded perspective view of a medication pen according to an embodiment of the invention.

FIG. 2 is a perspective view of the medication pen of FIG. 1 with the pen needle assembly installed.

DETAILED DESCRIPTION OF THE INVENTION

Figure 3:
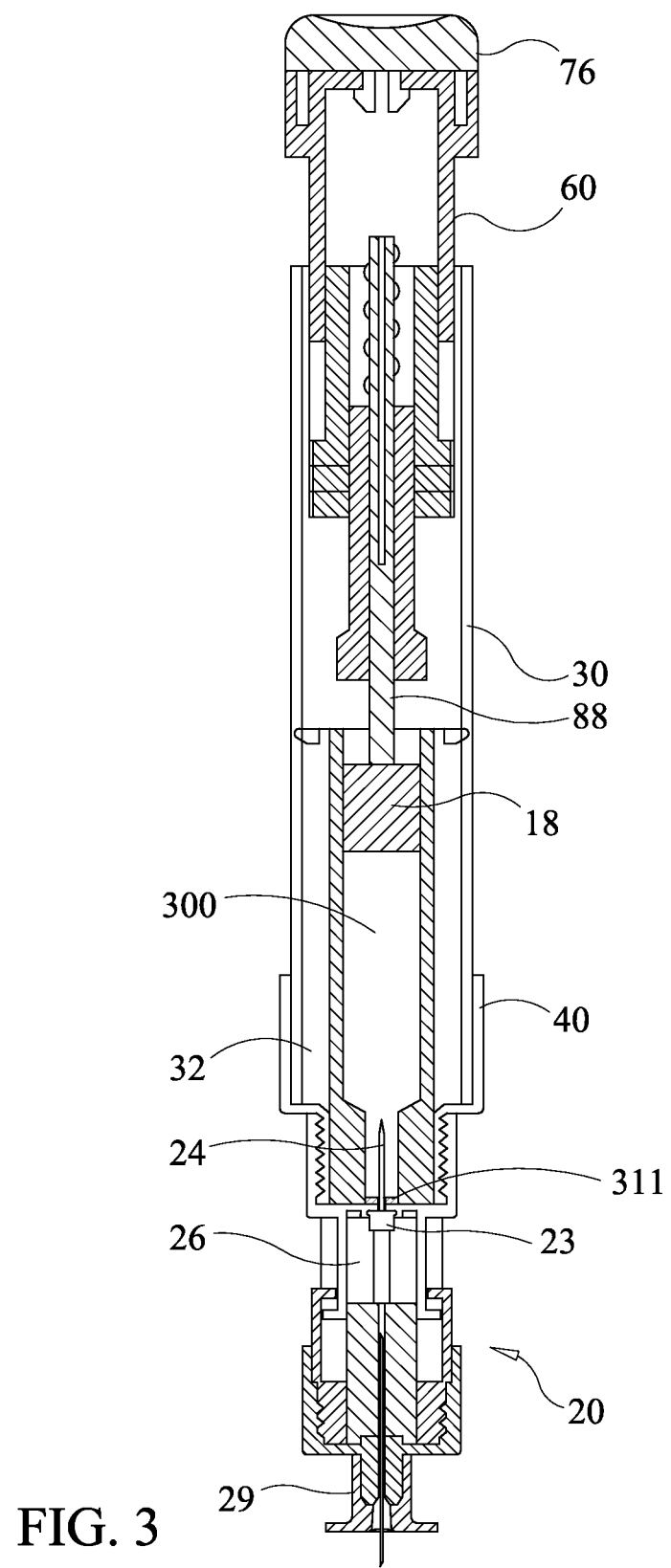
FIG. 3 is a cross-sectional view of the mixing medication pen according to an embodiment of the present invention.

In the following description, the "distal" direction is the direction toward the patient end needle and the injection site. The "proximal" direction is the opposite direction, typically but not necessarily toward the end of the injection device with the dosage knob. The drawings are not to scale.

A medication pen 100 according to the invention has a pen body 30, with at least two medication compartments 32, 34. A fillable pen needle assembly 20 is attached to a movable housing 40 on the distal end of the pen body. The movable housing 40 permits the pen needle assembly 20 to access the medication in each medication compartment 32, 34 as described below.

As seen in FIG. 1, the medication compartments 32, 34 can be arranged side by side in the pen body. Typically, disposable cartridge assemblies 300, 302 containing multiple doses of medication to be mixed and co-administered are inserted into the respective medication compartments 32, 34 of the medication pen. For example, a first cartridge containing insulin is provided in a first compartment and another cartridge containing GLP is provided in the second compartment. Access to the medication compartments may be provided by way of a door on the side of the pen body, or the cartridges can be slid axially into an opening on the distal end of the pen body, as shown in FIG. 1.

The medication compartments 32, 34 are associated with respective dosing mechanisms 200, 202. The medication compartments and dosing mechanisms are substantially identical, such that a description of one compartment and dosing mechanism will serve to describe both of them. Moreover, dosing mechanisms known in the art may be adapted for use with the present invention. Incorporated herein by reference for this purpose are U.S. Pat. No. 7,018,364 (Bendek et al.); U.S. Pat. No. 6,936,032 (Burbank et al.); U.S. Pat. No. 5,961,495 (Lee et al.); U.S. Pat. No. 6,585,698 (Packman et al.); U.S. Pat. No. 6,932,794 (Bendek et al.); U.S. Pat. No. 6,248,095 (Giambattista); U.S. Pat. No. 6,096,010 (Lee et al.); U.S. Pat. No. 6,277,099 (Strowe et al.); and U.S. Pat. No. 6,221,053 (Walters et al.).

Figure 5:
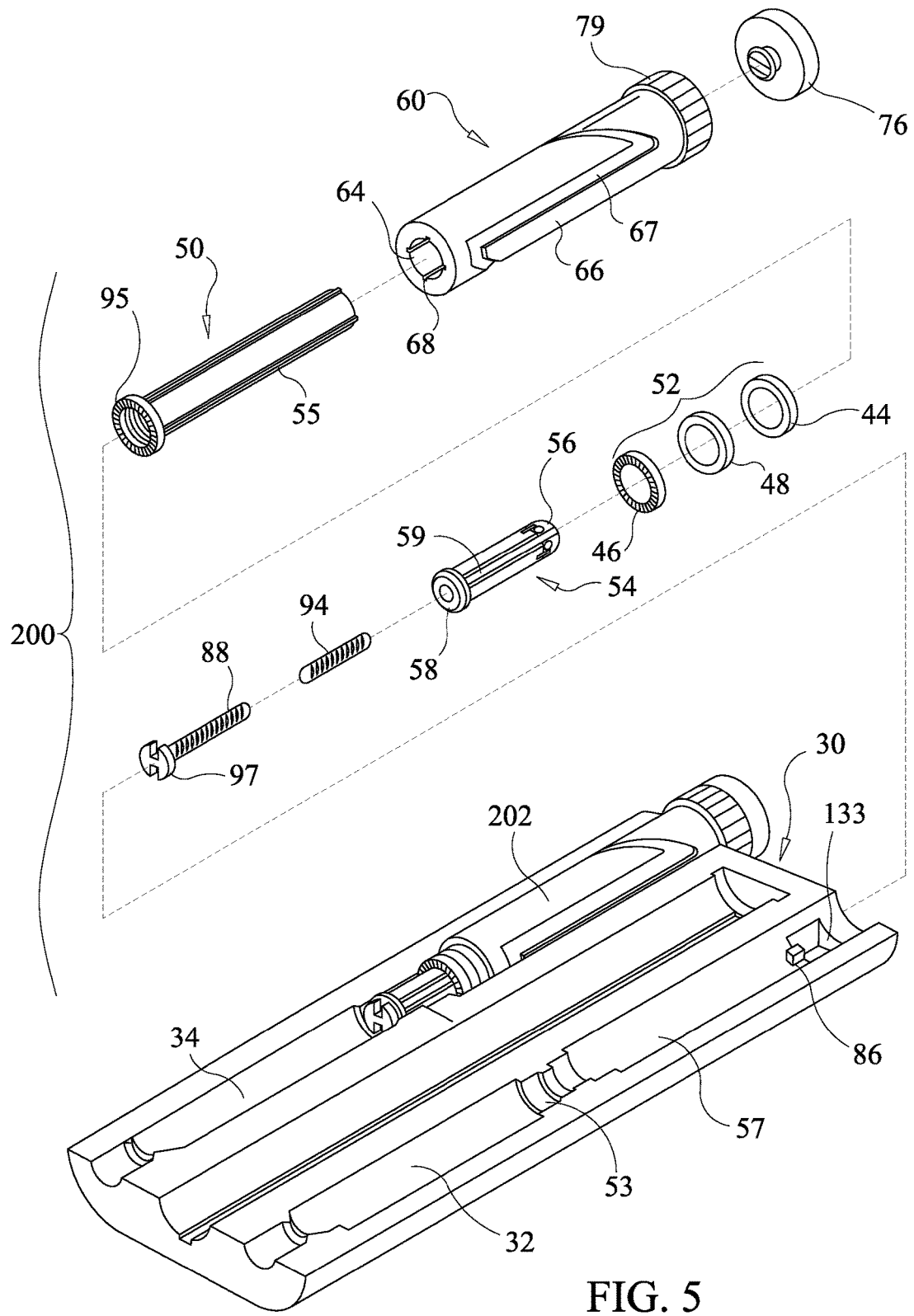
FIG. 5 is an exploded view of the medication pen showing the construction of the dosing mechanism according to an embodiment of the invention.

FIG. 5 shows the lower part of pen body 30 with the top removed to depict the position of the dosing mechanism chamber 57 and the medication compartment 32 in the pen body 30. Each medication compartment 32, 34 receives a medication cartridge assembly 300, 302 securely retained in an internal space of pen body 30. As shown in the cross sectional view of FIG. 3, medication cartridge assembly 300 includes an open proximal end and a distal end having an elastomeric seal 311 securely mounted thereto. A plunger 18 is disposed in sliding fluid tight engagement in the medication cartridge assembly 300. Plunger 18 initially is disposed substantially adjacent the proximal end of medication cartridge assembly 300. Moving the plunger in a distal direction forces medication from the medication cartridge assembly 300 into mixing reservoir 26 in the pen needle assembly. The plunger 18 of the cartridge assembly engages distal end of lead screw 88 of the dosage mechanism, as described below.

The dosing mechanism 200 for dosing and dispensing medication from the respective medication cartridges 300, 302 into the mixing reservoir 26 may be adapted from the abovementioned U.S. Pat. No. 5,542,760, which is incorporated by reference. As described in the aforesaid patent, and as shown in the exploded view of FIG. 5, a suitable dispensing mechanism is disposed distally of the medication compartment 34 and includes a nut 54 having opposed proximal and distal ends 56 and 58 respectively. Exterior surface regions of nut 54 define a plurality of longitudinally extending splines 59. Proximal end 56 of nut 54 is characterized by a plurality of longitudinally extending resilient fingers with enlarged ends that enable snap engagement of nut 54 into driver 50. Distal end 58 of nut 54 is radially enlarged to fit in a collar 53 in the pen body and limit axial movement of nut 54 in chamber 57.

Dosing mechanism 200 further includes a clutch assembly 52 mounted therein. Clutch assembly 52 includes a proximal clutch 44, a distal clutch 46 and an annular spring 48 biasingly engaged between the proximal and distal clutches. Proximal and distal clutches 44, 46 each are configured for non-rotatable engagement over splines 59 of nut 54. Distal clutch 46 includes an array of distally facing saw teeth dimensioned, disposed and configured for engagement with teeth on the interior of the pen body 30, such that distal clutch 46 can rotate only in one direction relative to the pen body 30.

Dosing mechanism 200 further includes a generally cylindrical driver 50 having opposed proximal and distal ends. Driver 50 receives nut 54, such that distal end of the driver 50 is snap fit over the enlarged ends of resilient fingers at proximal end of nut 54. This snap fit engagement prevents axial movement between nut 54 and driver 50, but permits free relative rotational movement within chamber 57. The distal end of driver 50 is also characterized by an array of saw teeth 95 that engage with corresponding teeth on proximal clutch 44. Outer surface regions of driver 50 are characterized by splines 55 extending radially outwardly thereon and along a substantial portion of the length of driver 50.

Dosing mechanism 200 further includes a dose knob 60 which is a hollow generally cylindrical structure. Inner surface 64 of the dosage knob 60 is characterized by axially extending grooves 68 which are disposed and dimensioned for engagement with splines 55 on driver 50. Dose knob 60 is spline mounted over driver 50 so that axially extending grooves 68 in dose knob 60 engage splines 55 of driver 50 to prevent relative rotation between the dosage knob and the driver, but permitting relative axial movement in chamber 57. Outer surface 66 of dose knob 60 is characterized by a groove 67 that includes an axial component and a tangential component at opposed ends of the axial component. Portions of outer surface 66 of the dosage knob are provided with dosage indicia (not shown) to define dose amounts corresponding to different positions along groove 67. Proximal end of dose knob 60 is characterized by a gnarled exterior surface to facilitate manipulation for setting a selected dose, and may include indicia 79 to facilitate setting the dosage knob at a particular setting. An actuator button 76 is snapped in to engage with proximal end of dose knob 60 while permitting relative rotation of the dose knob 60 with respect to the actuator button 76.

Inner surface of chamber 57 includes a button 86 dimensioned and disposed to engage in groove 67 of dose knob 60. Window 133 is disposed to enable indicia on dose knob 60 to be visible to the user as dose knob 60 is rotated and button 86 travels along groove 67.

Dosing mechanism 200 further includes a lead screw 88 with opposed proximal and distal ends, and an array of external threads 94. Threads 94 are engaged in nut 54, such that proximal end of lead screw 88 is within chamber 57 and a driver head 97 at the distal end of the lead screw projects distally beyond collar 53 into the medication compartment, where it engages the plunger 18 of the medication cartridge.

Dosing mechanism 200 is assembled by sliding clutch assembly 52 over splines 59 on nut 54. Driver 50 is then sufficiently urged onto nut 54 in a distal direction for snap fit engagement with nut 54. In this snapped engagement, proximal clutch 44 will be engaged with distal end of driver 50. Spring 48 will maintain constant selected pressure between the clutch and the driver. Dose knob 60 is then slid onto driver 50, and actuator button 76 is snapped into engagement with proximal end of dose knob 60. Lead screw 88 is threaded into nut 54.

Assembled dispensing mechanisms 200 and 202 are inserted into respective chambers in pen body 30 proximally of the respective medication compartments 32, 34.

The details of the dosing and dispensing mechanism described above are not critical and other mechanisms described in the prior art may be adapted for use with the mixing pen according to the present invention provided that the mechanisms permit the user to dispense a predetermined amount of medication into the mixing reservoir of the pen needle assembly as described below. For example, the invention is described above in connection with a user operated dose setting mechanism, but the dosing mechanism could also be adapted to dispense a predetermined amount of medication into the mixing reservoir from each medication compartment without the user setting a dose.

Further, the term "medication pen" is used herein broadly to refer to any injection device other than a syringe. A medication pen differs from a syringe in that it is adapted for use with pre-packaged medication so that the user does not have to withdraw medication from a vial using the syringe. As understood in the art, a "pen needle" and a "pen needle assembly" refer to an assembly that is attached to the body of a medication pen. As distinguished from a syringe, a pen needle assembly is characterized by a filler needle on the proximal end of the assembly to access the medication compartment in the body of the medication pen. The use of the term "pen" does not imply any limitation regarding the shape or construction of the injection device, such as the placement of the actuator on the proximal end of the device.

To prepare for a mixing operation, the user screws the fillable pen needle assembly 20 onto the movable housing 40 on the distal end of the pen body 30. Threads may be provided on the housing for this purpose. In the embodiment shown In FIG. 1, movable housing 40 is provided with an externally threaded opening 43 protruding from a distal end of the housing 40. The opening allows threaded attachment of pen needle assembly 20 with the movable housing 40. As shown in FIG. 2, when moved in the proximal direction, movable housing 40 slides over pen body 30 so that a filler needle can access one or the other of medication compartments 32 and 34. Alternatively, pen needle assembly 20 is provided with external threads, and the movable housing 40 provided with an opening having internal threads. This allows selective engagement of the pen needle assembly with the medication compartment 32, 34 via the movable housing without adding length to the movable housing. Other configurations would be apparent to those of ordinary skill in the art, such as a recessed opening on the distal end of the movable housing adapted to receive the proximal end of the pen needle assembly and provide access to the medication compartment. For example, the pen needle may be adapted for a snap fit engagement with an appropriate opening in the movable housing 40. It may be desirable in some embodiments to have the entire pen needle assembly formed integrally with the movable housing 40.

After the pen needle assembly 20 is installed on the movable housing 40 and the filler needle is inserted into the first medication compartment in the first position, the user sets and activates the dosing mechanism 200 to fill a predetermined quantity of a first medication into the mixing reservoir 26 of the pen needle assembly 20.

Figure 4:
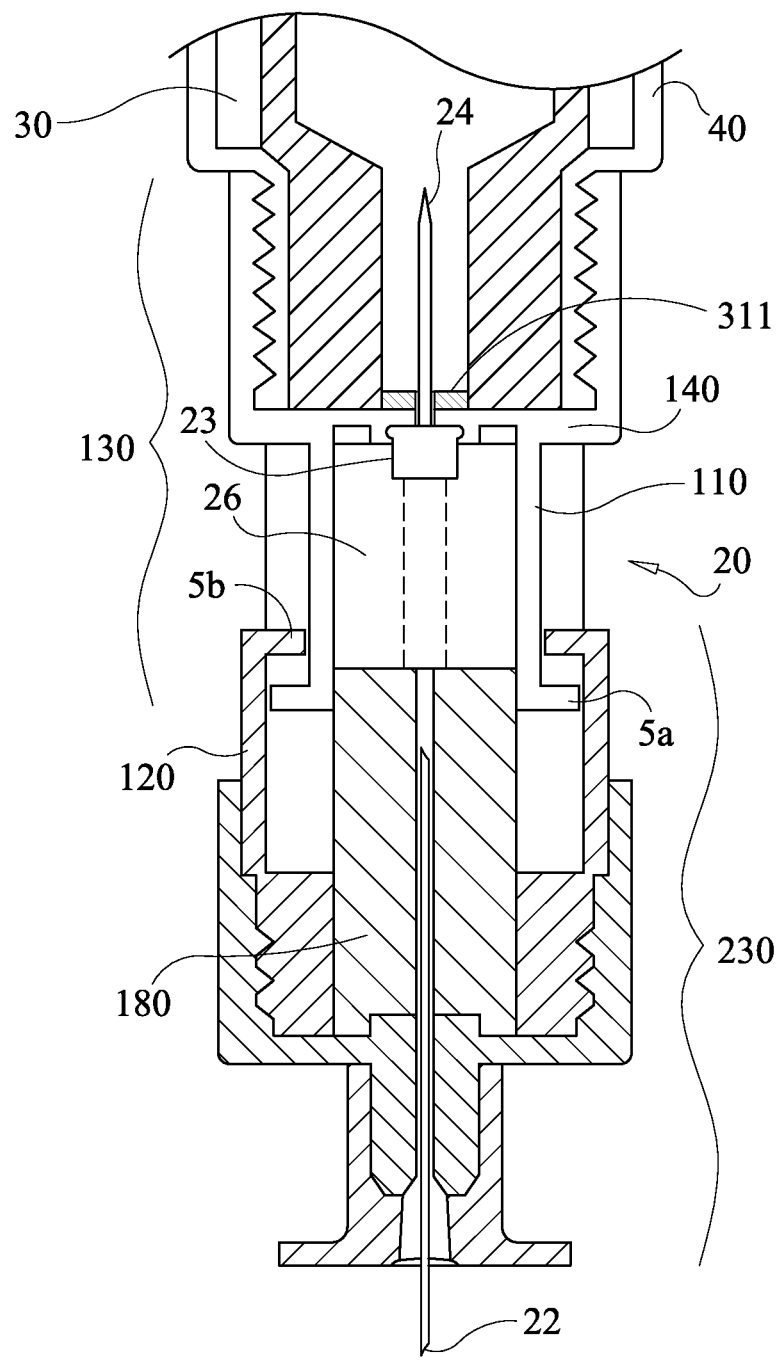
FIG. 4 is an enlarged cross sectional view of a pen needle assembly according to an embodiment of the invention.

As seen FIG. 3 and FIG. 4, the fillable pen needle assembly 20 has a patient end needle 22 for performing the injection, a filler needle 24 to access the medication compartments 32, 34 and a collapsible mixing reservoir 26 between the patient end needle 22 and the filler needle 24. As commonly practiced in the art, the pen needle assembly 20 may be disposable, while the cartridge contains medication for several doses. The pen body and dosing mechanisms typically last the lifetime of the cartridge or longer. The pen needle assembly may comprise a first removable cover (not shown) on the patient end needle 22 which is removed prior to administering an injection and a second removable cover (not shown) over the filler needle 24 which is removed prior to installing the pen needle assembly on the movable housing 40. In embodiments, a disposable needle stop 29 is separately installed on the pen needle assembly 20 such that the patient end needle with its integral support is adapted for one time use, while the mixing reservoir 26 of the pen needle assembly is used multiple times.

As shown in FIGS. 1 and 2, the movable housing 40 is movable in a proximal direction so that filler needle 24 pierces septum 311 of the medication cartridge 300 of a first medication compartment 32 in a first position. In the embodiment of FIG. 1 and FIG. 2, the movable housing 40 is attached to pen body 30 via shaft 62 which slides into pen body 30. Shaft 62 permits the housing 40 to be moved distally from the first position on the pen body, withdrawing the filler needle 24 from the medication compartment 32 without completely separating the pen needle assembly 20 from the pen body. Shaft 62 and movable housing 40 may then be rotated 180 degrees so that the pen needle assembly 20 is aligned with the second medication compartment 34. The movable housing 40, with the pen needle assembly 20 attached, is then moved proximally to a second position where the filler needle pierces the septum of a cartridge in the second medication compartment. Travel stops (not shown) may be provided on the shaft 62, engaging with stops (not shown) on the interior of the pen body 30, limiting the distal and proximal movement and rotation of the housing about the shaft to assist the user to place the pen needle assembly 20 in alignment with the respective medication compartments 32, 34. While the rotating housing is a presently preferred embodiment for the movable housing, other modes of moving the housing from a first position to a second position are within the skill of the ordinarily skilled artisan to adapt. Further, the pen body 30 may be constructed so as to permit medication compartments 32 and 34 to be moved with respect to the dosing mechanism. Thus, pen body 30 may be rotatable about a shaft so that a single dosing mechanism is used for multiple steps of filling mixing reservoir 26.

In the embodiment depicted in the cross-sectional view of FIG. 3, pen needle assembly 20 is shown attached to housing 40 on the distal end of pen body 30. Pen needle assembly 20 includes patient end needle 22, and filler needle 24, which accesses cartridge assembly 300 in medication compartment 32 located within the pen body 30. In the cross sectional view, only one medication compartment is shown, however, the details are the same for each medication compartment. Typically, the medication compartment 32 is adapted to receive a cartridge or other medication receptacle. However, in some applications, it may be desirable to maintain the medicament within the medication compartment without the use of a separate cartridge. As used herein, the "medication compartment" encompasses the compartment with a cartridge included, unless the context requires otherwise.

The pen needle assembly 20 includes collapsible mixing reservoir 26 intermediate the medication compartment 32 and the patient end needle 22. The filler needle 24 includes septum penetrating cannula penetrating the cartridge septum 311 and an opposite end accessing the collapsible mixing reservoir 26. Preferably, check valve 23 allows fluid to flow from the medication compartment into the mixing reservoir 26, but prevents fluid from entering either of medication compartment 32, 34 from the mixing reservoir 26. The patient-end needle 22 is supported on needle stop 29 and has a first proximal end accessing the collapsible mixing reservoir and a distal patient end.

Referring to the enlarged detail of FIG. 4, the pen needle assembly 20 comprises a proximal portion 130 attached to the movable housing 40 which is secured on pen body 30. Proximal portion 130 slides within distal portion 230. The proximal portion 130 comprises an opening for attachment to housing 40 via threads or other means, a medial wall 140 supporting the filler needle 24, and mixing reservoir wall 110 extending distally from the medial wall 140. The mixing reservoir wall 110 terminates in travel limits 5a which limit the travel of the distal portion 230 with respect to the proximal portion 130. The distal portion comprises a front sleeve 120 and a sliding seal 180 affixed to the distal portion 230, sliding within and sealing off mixing reservoir 26. Travel limits 5b engage travel limits 5a on the reservoir wall to prevent distal movement of the distal portion 230 beyond a predetermined point. The volume of the mixing reservoir 26 expands to a fully filled state when the travel limits 5a and 5b of the proximal portion 130 and distal portion 230, respectively, contact one another. The travel limits 5a, 5b are preferably 90 degree flanges on the exterior walls of the front sleeve 120 and reservoir wall 110, respectively. A sliding seal 180 receives the proximal end of the patient needle 22 and extends into reservoir 26. The proximal end of the sliding seal 180 slides within the mixing reservoir 26, while the exterior wall 110 of mixing reservoir 26 fits between the interior wall of the front sleeve 120 and the sliding seal 180.

With the exception of the patient needle 22 and the septum penetrating cannula 24, the moving parts of the needle assembly 20 are preferably made from plastic by injection molding or other suitable process. The patient needle 22 and septum penetrating filler needle 24 may be made of surgical-quality metals, such as stainless steel. The septum penetrating filler needle 24 and check valve 23 may be secured in place by snap-fitting, interference-fitting, adhesives, welding or other means known in the art.

To perform the mixing operation, the user selects an amount of medication to be delivered from the first compartment by turning the dosage knob 60 on the first dosage mechanism, which limits the stroke of the lead screw 88 and plunger 18. The user then advances the dose knob toward the pen body. The relative movement of the dose knob causes the lead screw and plunger to move toward the pen needle assembly 20. During this "loading stroke," the plunger, which abuts the lead screw, passes through the medication compartment (typically, within the cartridge) and drives medicament from the cartridge assembly 300 into the mixing reservoir 26. As described above, the movable housing 40 with the pen needle attached is moved distally to disengage the filler needle 24 from the first medication compartment 32, rotated to align the filler needle with the second medication compartment 34, and moved proximally to engage the filler needle 24 with the second medication compartment.

To perform an injection, the device is placed on the patient's skin such that the needle is seated into the tissue. The patient needle 22 is inserted into the skin as far as the needle stop, with mixing reservoir 26 partially closed. It will be appreciated that the needle length and gauge can be modified depending on whether the injection is being applied subdermally, intradermally, or intravenously, for example. Once the needle stop 29 is seated on the skin, a downward force is applied to the device by grasping the outer sleeve. The force exerted on the outer sleeve drives the housing toward the needle stop 29. This movement causes axial movement of the seal 180 within the mixing reservoir towards the medial wall 140, thus, collapsing the volume of the mixing reservoir 26 and causing the check valve to seal the pathway between the cartridge and the mixing reservoir 26. In the process of collapsing the volume of the mixing reservoir 26, the device 100 pressurizes the medicament in the mixing reservoir 26, thereby driving it through the patient needle 22.

The above description of the preferred embodiments is not to be deemed limiting of the invention, which is defined by the following claims. The foregoing description should provide the artisan of ordinary skill with sufficient information to practice variants of the embodiments described. Features and improvements described in connection with one embodiment may be combined with other embodiments without departing from the scope of the invention.

What is claimed is:

1. A medication pen comprising:
   a pen body having a distal end and a proximal end, and having a first medication compartment and a second medication compartment;
   first and second dosing mechanisms and first and second dosage plungers engaged in the respective first and second medication compartments;
   a movable housing received on the distal end of the pen body adapted to be received in first and second positions on the pen body;
   a pen needle assembly received on the distal end of the movable housing, said pen needle assembly comprising a patient end needle, a filler needle, and a collapsible mixing reservoir intermediate and accessed by said patient end needle and said filler needle;
   wherein the movable housing is movable between a first position in which the filler needle is in fluid communication with the first medication compartment and a second position in which the filler needle is in fluid communication with the second medication compartment; and
   wherein collapsing the mixing reservoir forces medication in the mixing reservoir through the patient end needle during an injection.

2. The medication pen according to claim 1, wherein each medication compartment comprises a medication cartridge and each dosage plunger engages a respective medication cartridge.

3. The medication pen according to claim 1, further comprising a check valve on the filler needle preventing backflow from the mixing reservoir into the first and second medication compartments.

4. The medication pen according to claim 1, wherein the first and second dosing mechanisms comprise first and second rotatable knobs protruding from the proximal end of the pen body.

5. The medication pen according to claim 1, wherein the movable housing is connected to the pen body by a shaft having a longitudinal axis, the shaft being disposed to slide into the pen body, and the movable housing is rotatable about the axis of the shaft, from a first position in which the filler needle is axially aligned with the first medication compartment to a second position in which the filler needle is axially aligned with the second medication compartment.

6. The medication pen according to claim 1, wherein the collapsible mixing reservoir includes a stopper moving within and sealing the mixing reservoir, wherein the patient end needle extends through the stopper to access the mixing reservoir, and wherein a sleeve on the exterior of the pen needle assembly is secured to the stopper, so that moving the sleeve in a proximal direction moves the stopper to collapse the mixing reservoir, forcing medication out of the patient end needle.

7. The medication pen according to claim 1, wherein the first medication compartment contains insulin and the second medication compartment contains GLP.

8. The medication pen according to claim 1, including a recessed opening on a distal end of the movable housing adapted to receive the proximal end of the pen needle assembly to provide access to the medication compartment.

9. The medication pen according to claim 1, including a threaded opening protruding from a distal end of the movable housing adapted to receive an internally threaded opening on a proximal end of the pen needle assembly.

10. The medication pen according to claim 1, comprising a shaft connecting the movable housing and the pen body, said shaft sliding proximally and distally in the pen body from a proximal position in which the filler needle of the pen needle assembly is engaged in one of said medication compartments and a distal position in which the pen needle assembly rotates with respect to the pen body, such that a pen needle installed on the movable housing is moved from a first position in which the filler needle is in fluid communication with the first medication compartment and a second position in which the filler needle is in fluid communication with the second medication compartment.

11. The medication pen of claim 1, wherein the pen needle assembly comprises a first removable cover on the patient end needle which is removed prior to administering an injection.

12. The medication pen of claim 1, wherein the pen needle assembly comprises a second removable cover on the filler needle which is removed prior to installing the pen needle assembly on the movable housing.

13. The medication pen according to claim 1, comprising a shaft connecting the movable housing and the pen body, the shaft sliding proximally and distally in the pen body from a distal position in which first and second medication cartridges can be respectively inserted proximally into said first and second medication compartments in the pen body, to a proximal position in which the filler needle of the pen needle assembly is engaged in one of said medication compartments.

* * * * *